United States Patent
Parry et al.

(10) Patent No.: US 6,453,197 B1
(45) Date of Patent: Sep. 17, 2002

(54) IMPLANTABLE CARDIAC STIMULATION DEVICE INCLUDING A SYSTEM FOR AND METHOD OF AUTOMATICALLY INDUCING A TACHYARRHYTHMIA

(75) Inventors: John Thomas Parry, Northville; Gary Robert Viviano, Brighton, both of MI (US); James Edward Gantz, Jr., Cincinnati, OH (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/552,299

(22) Filed: Apr. 18, 2000

(51) Int. Cl.[7] ................................................. A61N 1/18
(52) U.S. Cl. ...................................................... 607/14
(58) Field of Search ................................ 600/509, 515, 600/518, 519; 607/9, 11, 14, 28, 60, 119

(56) References Cited

U.S. PATENT DOCUMENTS

| | | | |
|---|---|---|---|
| 4,390,021 A | * 6/1983 | Spurrell et al. | ............ 128/419 |
| 4,686,988 A | 8/1987 | Sholder | ............... 128/419 PT |
| 4,708,142 A | 11/1987 | Decote, Jr. | ............ 128/419 PT |
| 4,712,555 A | 12/1987 | Thornander et al. | .. 128/419 PG |
| 4,729,376 A | 3/1988 | Decote, Jr. | ............ 128/419 PT |
| 4,788,980 A | 12/1988 | Mann et al. | .......... 128/419 PG |
| 4,940,052 A | 7/1990 | Mann et al. | .......... 128/419 PG |
| 4,944,298 A | 7/1990 | Sholder | ................ 128/419 PG |
| 4,969,467 A | 11/1990 | Callaghan et al. | ..... 128/419 PG |
| 5,350,410 A | 9/1994 | Kleks et al. | .................. 607/28 |
| 5,653,740 A | 8/1997 | Degroot et al. | ................ 607/72 |
| 5,899,929 A | * 5/1999 | Thompson et al. | ........... 607/28 |
| 5,925,067 A | 7/1999 | Lu | ............................... 607/28 |

* cited by examiner

Primary Examiner—Jeffrey R. Jastrzab
Assistant Examiner—Frances P. Oropeyen

(57) ABSTRACT

A system and method for use in an implantable cardiac stimulation device permits automatic induction of a tachyarrhythmia of a heart to permit the performance of an electrophysiological test of the heart. A pulse generator repeatedly delivers a group of first and second sets of pacing pulses to a chamber of the heart. The pacing pulses are separated in time by interpulse intervals to overdrive pace a chamber of the heart. A processor, coupled to the pulse generator, varies the second set of interpulse intervals according to a predetermined protocol after each group of pacing pulses is delivered to the chamber of the heart. The successive groups of pacing pulses are delivered to the heart until the tachyarrhythmia is induced.

30 Claims, 3 Drawing Sheets

IMPLANTABLE CARDIAC STIMULATION DEVICE INCLUDING A SYSTEM FOR AND METHOD OF AUTOMATICALLY INDUCING A TACHYARRHYTHMIA

FIELD OF THE INVENTION

The present invention generally relates to an implantable cardiac stimulation device. The present invention more particularly relates to such a device which includes a system for and implements a method of automatically conducting a non-invasive programmed stimulation (NIPS) procedure for inducing a tachyarrhythmia of a heart to permit the performance of electrophysiological studies.

BACKGROUND OF THE INVENTION

Frequently, a clinician must perform electrophysiological studies in patients having implanted permanent pacemakers or cardioverters/defibrillators to determine accurately the patient's pathological condition, cardiovascular characteristics and other information needed in order to prescribe a particular therapeutic treatment for the patient. Such studies often require the inducement of a tachyarrhythmia of the heart such as ventricular tachycardia.

Originally, these studies were invasive because they required the surgical insertion of instruments such as temporary intracardiac pacing catheters into the patient. Thus, these studies were accompanied by some risk and preferably were performed in hospitals. Therefore, these studies were not only expensive, but also time consuming and caused patient anxiety.

In order to avoid medical risks to the patient and hospitalization, non-invasive programmed stimulation (NIPS) procedures have been developed to permit the electrophysiological studies to be performed in a physician's office during routine follow-up visits.

These procedures utilize the implanted cardiac stimulation device and an external programmer. By virtue of the presence of a permanent pacing/defibrillation lead associated with the implanted cardiac stimulation device, the need for placement of a temporary intracardiac pacing catheter is eliminated. Typically, NIPS procedures consist generally of the application of premature electrical pulses at precise intervals to the myocardium of the patient's heart by the implanted cardiac stimulation device and its associated lead or leads. The implanted device applies the stimulation pulses under commands from the external programmer which is manually controlled by the clinician. Prior to the procedure, the clinician manually defines the intervals between the successive stimulation pulses on the programmer. After the implanted device applies the succession of stimulation pulses to the heart, the clinician then, on the programmer, manually observes results such as tachyarrhythmia induction or lack of capture by the stimulation pulses. Thereafter, the clinician alters the stimulation pulse intervals and causes the programmer to initiate another application of the successive stimulation pulses to the patient's heart by the implanted cardiac stimulation device. As a result, NIPS studies, as currently constituted, are tedious to administer, consume considerable time, and lead to considerable cost to the electrophysiology laboratory.

SUMMARY OF THE INVENTION

The present invention provides a system and method for use in an implantable cardiac stimulation device that automatically induces a tachyarrhythmia of a heart to permit the performance of an electrophysiological test of the heart. In accordance with the present invention, the system and method permits the implantable cardiac stimulation device to perform a NIPS procedure automatically once initial parameters are established in the device by an external programmer under control of a clinician.

In accordance with the present invention, a NIPS protocol is stored in a memory within the implantable cardiac stimulation device. A processor accesses the NIPS protocol stored in the memory to control a pulse generator that repeatedly delivers groups of pacing pulses to a chamber of the heart. The pacing pulses are separated in time by pacing or interpulse intervals to overdrive pace the patient's heart. After each group of pacing pulses is delivered to the heart, the processor varies the pacing intervals according to the NIPS protocol prior to reinitiating the delivery of the next group of stimulation pulses. The processor terminates the delivery of the stimulation pulses if it detects the tachyarrhythmia of the heart after a group of stimulation pulses have been delivered to the heart.

In accordance with a further aspect of the present invention, the processor, in accordance with the NIPS protocol, determines capture of the heart by each delivered stimulation pulse and terminates the delivery of the stimulation pulses to the heart by the pulse generator when a predetermined number of successive pacing pulses fail to capture the heart. In accordance with a still further aspect of the present invention, the processor requires a minimum pacing interval to determine capture of the heart by a stimulation pulse. In accordance with the NIPS protocol, the processor terminates the delivery of the stimulation pulses to the heart when a pacing interval falls below the minimum pacing interval.

In accordance with still further aspects of the present invention, each group of stimulation pulses includes a first set of pulses employed to capture the heart at an overdrive pacing rate and a second set of pulses to induce the tachyarrhythmia. The processor, in accordance with the NIPS protocol, varies the pacing intervals of the second set of pacing pulses between the application of the groups of stimulation pulses.

In accordance with still further particular aspects of the present invention, the second set of pacing pulses includes a last pulse and a second to the last pulse and the processor decrements the pacing interval between the last pulse and the second to the last pulse responsive to the last pulse capturing the heart in accordance with the NIPS protocol. Further, the second set of pacing pulses further includes a third to the last pulse. The processor, in accordance with the NIPS protocol, decrements the pacing interval between the second to the last pulse and the third to the last pulse and resets the pacing interval between the last pulse and the second to the last pulse to an initial interval responsive to the last pulse failing to capture the heart.

The application of the successive groups of pacing pulses is automatically continued with intergroup pacing interval adjustment until the tachyarrhythmia is detected by the processor. The procedure may further be terminated if manually terminated by the clinician, if a predetermined number of pacing pulses fail to capture the heart, or if a pacing interval falls below the minimum interval required by the processor to determine capture of the heart.

BRIEF DESCRIPTION OF THE DRAWINGS

Further features and advantages of the present invention may be readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
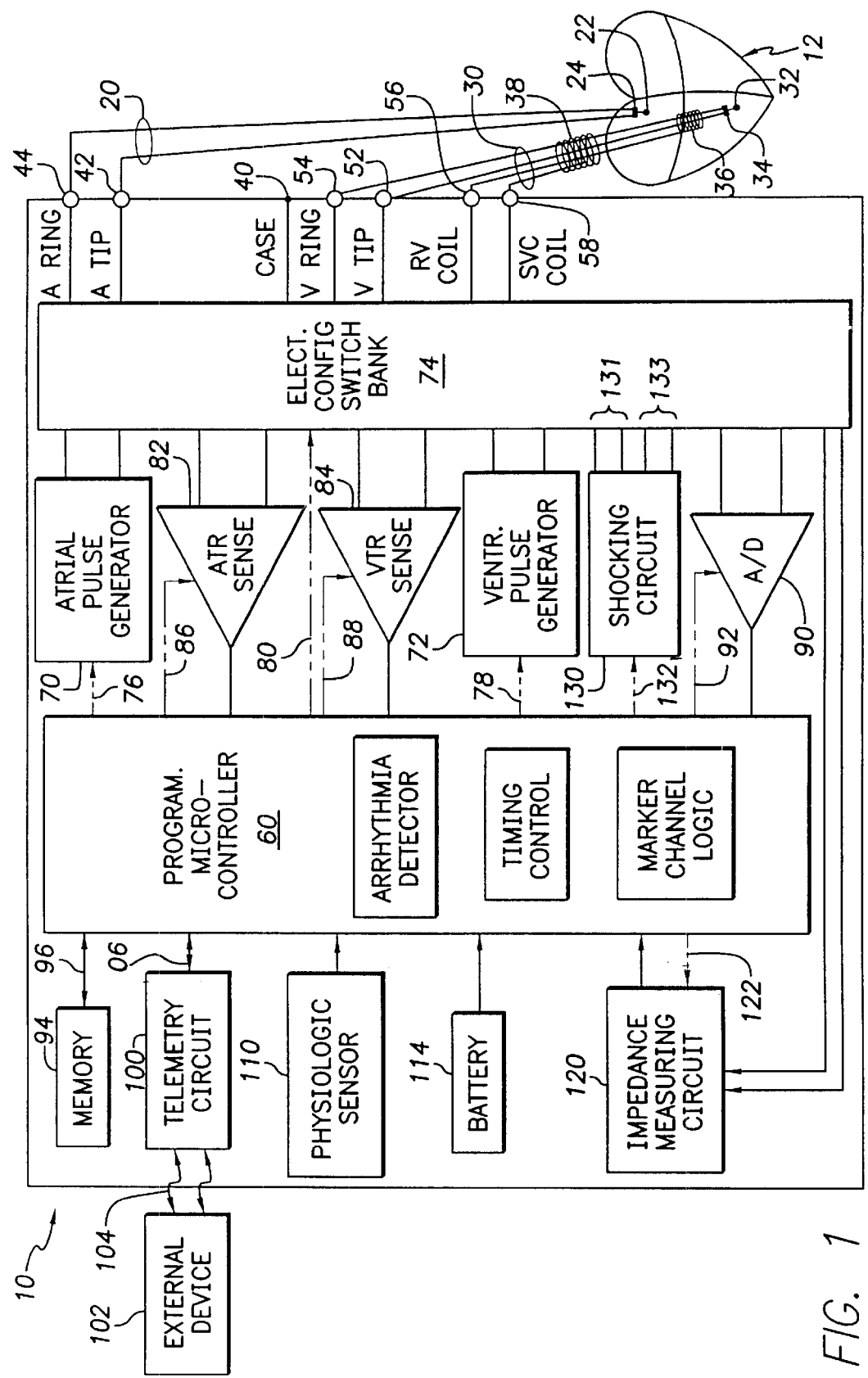
FIG. 1 is a functional block diagram of a dual-chamber implanted stimulation device illustrating the basic elements of a stimulation device which can provide cardioversion, defibrillation, and pacing stimulation, which device embodies and may utilize the present invention to advantage.

In FIG. 1, a simplified block diagram is shown of a dual-chamber implantable stimulation device 10 embodying the present invention and which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation.

The housing 40 (shown schematically) for the stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a ventricular tip terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

The stimulation device 10 further includes a programmable microcontroller 60 which controls the various modes of stimulation therapy including a non-invasive programmed stimulation (NIPS) procedure in accordance with the present invention. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. Representative types of control circuitry that may be used for embodying the invention include the microprocessor-based control system of U.S. Pat. No. 4,940,052 (Mann et al.), the state-machine of U.S. Pat. No. 4,712,555 (Sholder) and U.S. Pat. No. 4,944,298 (Sholder). For a more detailed description of the various timing intervals used within the stimulation device and their interrelationship, see U.S. Pat. No. 4,788,980 (Mann et al.). The '052, '555, '298 and '980 patents are incorporated herein by reference. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses (e.g., pacing rate and atrioventricular (AV) delay), as well as keeping track of the timing of any refractory periods, PVARP intervals, noise detection windows, evoked response windows, alert intervals, marker channel timing, etc., that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the device 10 utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P-P and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy"). In accordance with the present invention, the microcontroller 60 may employ a high rate classification to determine if a tachyarrhythmia is present for terminating the NIPS procedure when the tachyarrhythmia has been induced by the NIPS procedure.

Cardiac signals are also applied to the inputs of an analog to digital (A/D) data acquisition system 90. The data acquisition system 90 is configured to sense or acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The data acquisition system is preferably coupled to the microcontroller, or other detection circuitry, for detecting an evoked response from the heart 12 in response to an applied stimulus, thereby aiding in the detection of "capture". As will be seen hereinafter, capture detection is especially desirable in implementing a NIPS procedure. Capture occurs when an electrical stimulus applied to the heart is of sufficient energy and applied at an appropriate time in a cardiac cycle to depolarize the cardiac tissue, thereby causing the heart muscle to contract. The microcontroller 60 detects a depolarization signal during a window following a stimulation pulse, the presence of which indicates that capture has occurred. The microcontroller 60 may enable capture detection by starting a capture detection window when a ventricular stimulation pulse is issued using the timing circuitry within the microcontroller 60, and enabling the data acquisition system 90 via control signal 92 to sample the cardiac signal that falls in the capture detection window and, based on the amplitude, determines if capture has occurred. As is known in the art, this form of capture detection requires a minimum interpulse interval to sustain the window detection. Further, capture detection is preferably performed on a beat-by-beat basis during a NIPS procedure.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. The type of capture detection system used is not critical in the implementation of the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy. The memory 94 preferably also stores a NIPS protocol from which the microcontroller automatically controls the NIPS procedure.

The operating parameters of the implantable device 10, the NIPS protocol, and the NIPS initializing parameters or values may be non-invasively programmed into the memory 94 through a telemetry circuit 100 in telemetric communication with an external device 102, such as a programmer, transtelephonic transceiver, or a diagnostic system analyzer. The telemetry circuit 100 is activated by a control signal 106 from the microcontroller 60. The telemetry circuit 100 also allows intracardiac electrograms, status information relating to the operation of the device 10 (as contained in the microcontroller 60 or memory 94) to be sent to the external device 102 through the established communication link 104.

The stimulation device 10 further includes a physiologic sensor 110. Such sensors are commonly called "rate-responsive" sensors. The physiological sensor 110 is used to detect and generate a raw signal representing the activity of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits show in FIG. 1. For the stimulation device 10, which employs shocking therapy, the battery must be capable of operating at low current drains for long periods of time and then be capable of providing high-current pulses (for capacitor charging) when the patient requires a shock pulse. The battery 114 must also have a predictable discharge characteristic so that elective replacement time can be detected. Accordingly, the device 10 may employ lithium/silver vanadium oxide batteries, as is common in many such device to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data, including NIPS procedure initializing parameters to the microcontroller 60 through the telemetry circuits 100 or instructions to initiate or terminate a NIPS procedure.

As further shown in FIG. 1, the device includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock threshold; detecting when the device has been implanted; measuring stroke volume; and detecting the opening of the valves, etc. The impedance measuring circuit 120 is advantageously coupled to the switch bank 74 so that any desired electrode (including the RV and SVC coil electrodes, 36 and 38) may be used. The impedance measuring circuit 120 is shown only for completeness.

An important function of the device 10 is to function as an implantable cardioverter/defibrillator (ICD) device. That is, it is capable of detecting the occurrence of an arrhythmia, and automatically applying an appropriate electrical shock therapy to the heart aimed at terminating the detected arrhythmia. To this end, the microcontroller 60 further controls a shocking 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
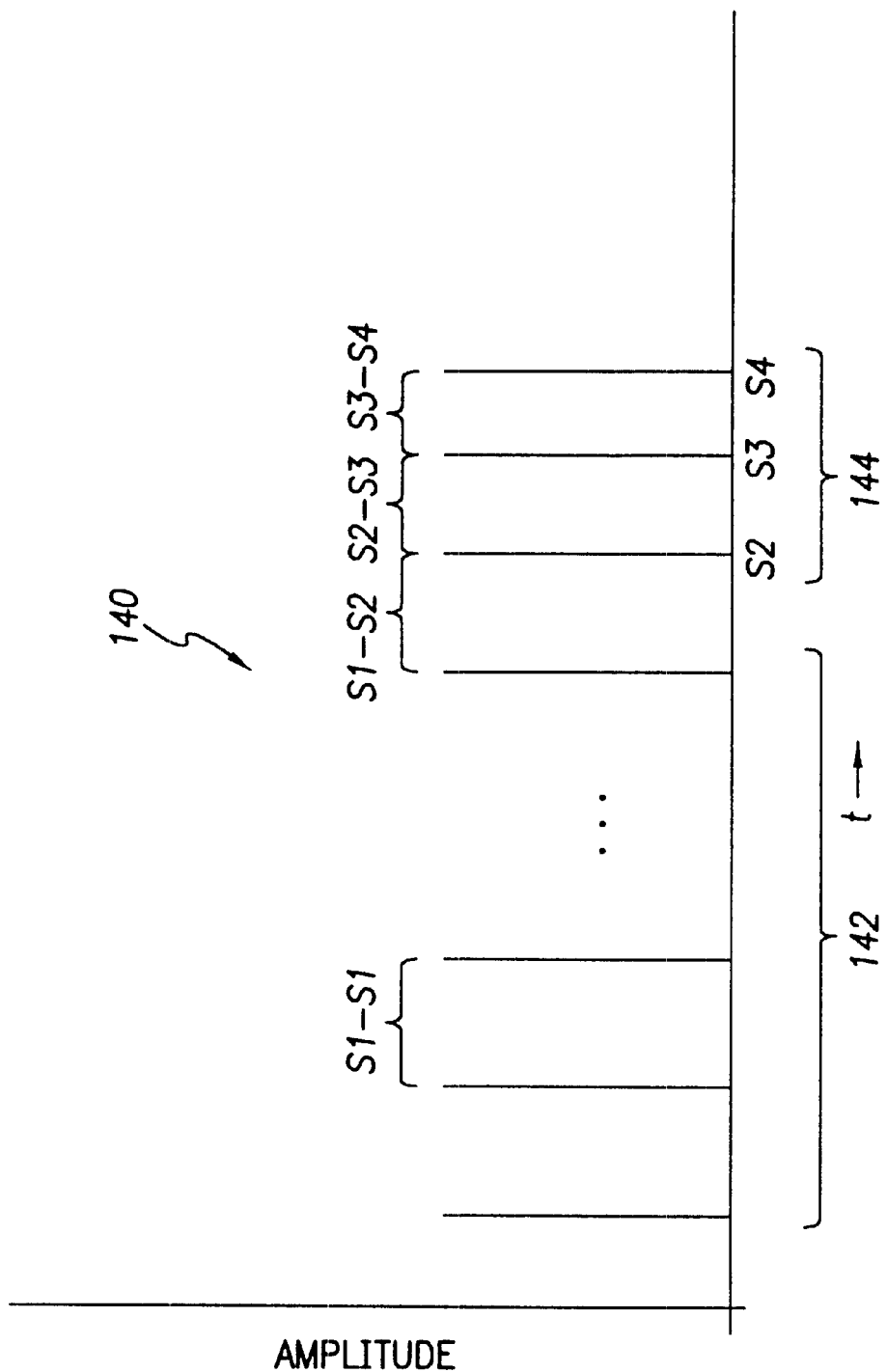
FIG. 2 shows one group of stimulation pulses which may be used for performing a NIPS procedure in accordance with the preferred embodiment of the present invention.

FIG. 2 illustrates a group 140 of stimulation or pacing pulses forming a pulse train which are provided to the right ventricle of the heart by the pulse generator 72 to implement a NIPS procedure in accordance with this preferred embodiment of the present invention. The group 140 of pulses includes a first set 142 of pulses and a second set 144 of pulses. Each pulse of the first set is referred to as an S1 pulse and may range in number from, for example, 3–20, the number of S1 pulses being a programmable parameter. Immediately successive S1 pulses have a programmable interpulse interval (S1—S1) on the order to 300–400 milliseconds to provide overdrive pacing of the heart. Each S1 pulse also preferably has a programmable amplitude and pulse width of, for example, 4.5 volts (v) and 0.5 milliseconds, respectively, to assure capture of the heart by each S1 pulse. It is the purpose of the first set 142 of pulses to overdrive capture the heart.

The second set 144 of pulses, commonly referred to as the extra pulses, includes pulse S2, pulse S3, and pulse S4. The number of extra pulses may also be a programmable parameter and vary from that described herein. Each of the S2, S3, and S4 pulses also preferably has a programmable amplitude and pulse width of, for example, 4.5 V and 0.5 milliseconds, respectively. The last S1 pulse and the extra pulses are separated in time by interpulse intervals S1–S2, S2–S3, and S3–S4 which are progressively decreasing. The extra pulse interpulse intervals may be initially set by the programmer 102 and may be 280 milliseconds, 260 milliseconds, and 240 milliseconds, respectively. The intended purpose of the extra pulses is to place the last extra pulse, pulse S4, in accordance with this embodiment, in an overdriven cardiac cycle of the heart where the stimulated heart tissue is only partially refractory for inducing the tachyarrhythmia.

To place the pulse S4 as described above, the microcontroller 60 in accordance with this preferred embodiment and the stored NIPS protocol, adjusts or varies the interpulse intervals S2–S3, and S3–S4 in a prescribed manner after each group 140 of pulses is delivered to the heart. After each adjustment of the interpulse intervals, the pulse train is reinitiated and delivered to the heart. The foregoing process continues until the tachyarrhythmia is induced.

Figure 3:
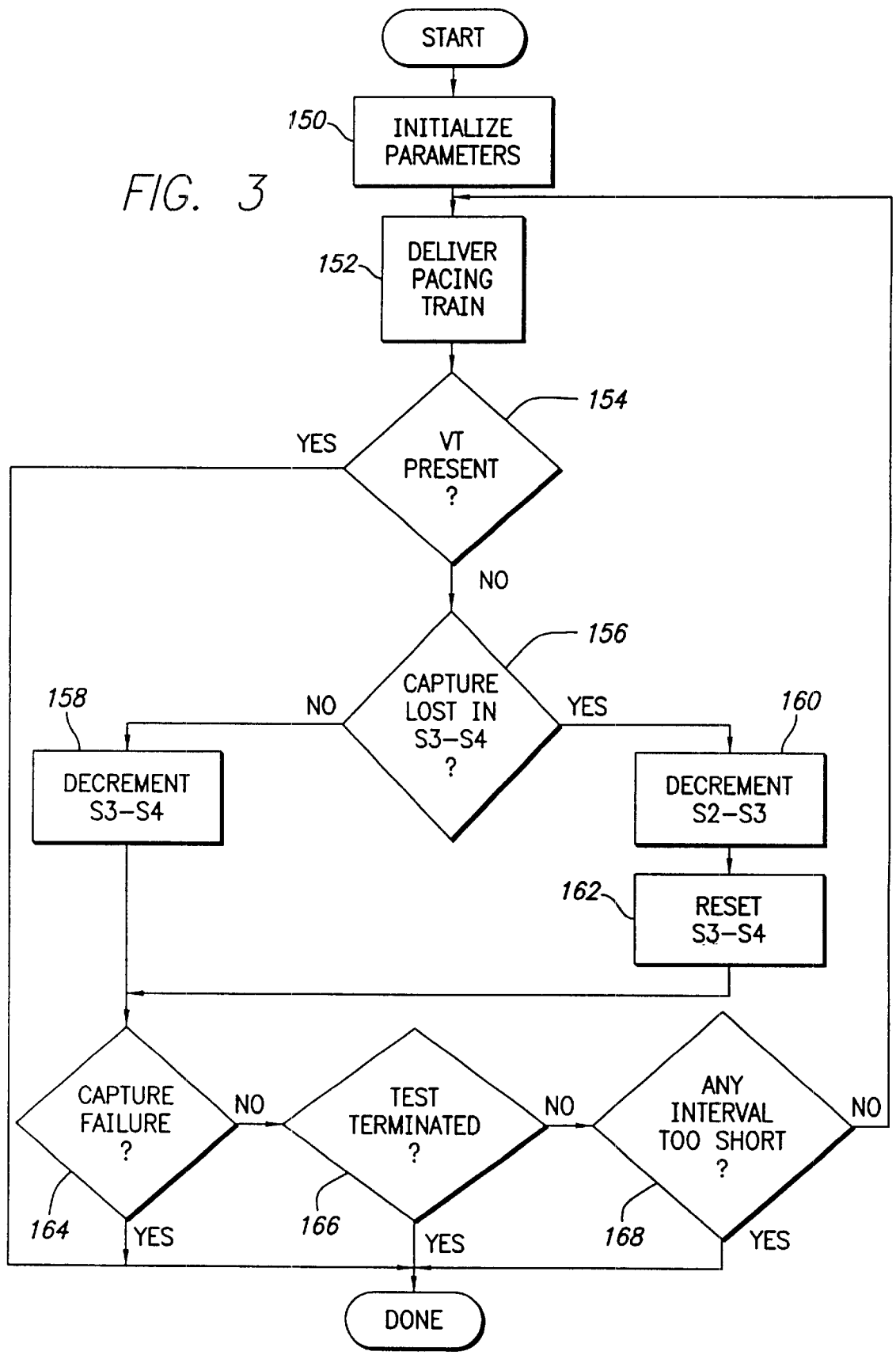
FIG. 3 shows a flow chart describing an overview of the operation of the device of FIG. 1 in accordance with the preferred embodiment of the present invention.

A prescribed manner in which the microcontroller 60 may vary the interpulse intervals and hence control the performance of the NIPS protocol of this embodiment is particularly illustrated in FIG. 3. In this flow chart, the various algorithmic steps are summarized in individual "blocks". Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates at an activity step 150 wherein initializing parameters are provided to the microcontroller 60 or memory 94 via the telemetry circuit 100. It is, of course, assumed that the NIPS protocol to be implemented has already been stored in the memory 94 in the same manner. The initializing parameters may be, for example, the initial S1–S1, S1–S2, S2–S3, and S3–S4 intervals, the amplitude and durations of the stimulation pulses, the time between successive pulse trains, and the interval by which each coupling interval will be decremented as called for by the protocol. Also, at this time, any normal automatic capture back-up pulse function is suspended while capture verification is enabled on a beat-to-beat basis.

After the initial parameters have been established, the process proceeds to activity step 152 wherein the microcontroller 60 causes the pulse generator 72 to deliver the first pulse train or first group of stimulation pulses as illustrated in FIG. 2 to the heart. After the first pulse train has been applied, the microcontroller next, in decision block 154 determines if the tachyarrhythmia has been induced. If the tachyarrhythmia is detected by the microcontroller, the process returns. However, if not, the process then advances to decision block 156. In decision block 156, the microcontroller determines if pulse S4 captured the heart. If pulse S4 captured the heart, the processor advances to activity step 158 to decrement the S3–S4 interpulse interval, by, for example, 10 milliseconds. If pulse S4 failed to capture the heart as determined in decision block 156, the process advances to activity blocks 160 and 162 in that order to decrement the S2–S3 interpulse interval and to reset the S3–S4 interval, if previously decremented, to its initial value. The process is now ready to reinitiate another pulse train with the adjusted intervals unless a termination condition exists to be described subsequently. Absence such a condition, the process will continue to adjust the interpulse intervals as described above after each pulse train. The pulse trains are reinitiated by the microcontroller until the tachyarrhythmia is detected in decision block 154.

After either activity block 158 are activity block 162 is completed, the microcontroller determines if a condition exists to terminate the NIPS procedure. The first such condition is illustrated by decision block 164 wherein the microcontroller determines if there has been a capture failure. More particularly, in accordance with this embodiment, such a capture failure is a condition wherein a predetermined number of consecutive stimulation pulses have failed to capture the heart. A predetermined number of successive stimulation pulses failing to capture the heart may be, for example, two consecutive pulses. As previously mentioned, capture is preferably verified after each stimulation pulse. If capture fails it is noted by the microcontroller. In decision block 164, the microcontroller performs an analysis of the notations. If the notations indicate that two consecutive stimulation pulses failed to capture the heart, the process immediately returns.

The next termination condition is illustrated by decision block 166. Here, the microcontroller determines if the NIPS procedure has been manually terminated by the clinician initiating a command to terminate the procedure from the external programmer 102. Such a command is received through the telemetry circuit 100 of the device 10. If a termination command is given, it will be noted by the microcontroller upon receipt and will be acted upon when the process reaches decision block 166. If such a notation of termination is present when the process reaches decision block 166, the microcontroller will terminate the NIPS procedure by immediately returning.

Lastly, the final termination condition is illustrated by decision block 168. Here, the microcontroller determines if any one of the interpulse intervals has been decremented to such as extent as to be shorter than the minimum interval required to support a beat-by-beat capture determination. If an interpulse interval is too short, the process immediately returns. If no pulse intervals is too short, the process reverts to activity block 152 to initiate the delivery of the next pulse train.

From the foregoing, it may be seen that the present invention provides a new and improved procedure for inducing a tachyarrhythmia of the heart to support an electrophysiological study. The procedure, such as a NIPS procedure, may be used to induce either a ventricular or atrial tachyarrhythmia. Since the procedure is truly automated, the tachyarrhythmia may be induced in less time, with less anxiety to the patient, and with reduced clinical cost.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device, a system that automatically induces a tachyarrhythmia of a heart to permit the performance of an electrophysiological test of the heart, the system comprising:

a pulse generator that repeatedly delivers a group of first and second sets of pacing pulses to a chamber of the heart, the pacing pulses being separated in time by pacing intervals to overdrive pace the chamber; and a processor, coupled to the pulse generator, that varies the pacing intervals according to a predetermined protocol after each group of pacing pulses is delivered to the chamber of the heart.

2. The system of claim 1 wherein the processor is programmed to detect the tachyarrhythmia of the heart and to terminate the delivery of the pacing pulses to the heart by the pulse generator when a group of the pacing pulses has induced the tachyarrhythmia.

3. The system of claim 1 wherein the processor is programmed to determine capture of the heart by each delivered pacing pulse and to terminate the delivery of the pacing pulses to the heart by the pulse generator when a predetermined number of successive pacing pulses fail to capture the heart.

4. The system of claim 3 wherein the predetermined number is two.

5. The system of claim 3 wherein the processor requires a minimum pacing interval to determine capture of the heart by a pacing pulse and is further programmed to terminate the delivery of the pacing pulses to the heart by the pulse generator when a pacing interval falls below the minimum pacing interval.

6. The system of claim 1 wherein the processor is programmed to vary the pacing intervals of the second set of pacing pulses according to the predetermined protocol.

7. The system of claim 1 wherein the processor is programmed to determine capture of the heart by each delivered pacing pulse, wherein the second set of pacing pulses includes a last pulse and a second-to-the-last pulse, and wherein the processor is programmed to decrement the pacing interval between the last pulse and the second-to-the-last pulse responsive to the last pulse capturing the heart according to the predetermined protocol.

8. The system of claim 1 wherein the processor is programmed to determine capture of the heart by each delivered pacing pulse, wherein the second set of pacing pulses includes a last pulse, a second-to-the-last pulse, and a third-to-the-last pulse, and wherein the processor is programmed to decrement the pacing interval between the second-to-the-last pulse and the third-to-the-last pulse responsive to the last pulse failing to capture the heart according to the predetermined protocol.

9. The system of claim 8 wherein the pacing interval between the last pulse and the second-to-the-last pulse is preset to an initial interval prior to delivery of the pacing pulses to the heart by the pulse generator and wherein the processor is further programmed to set the pacing interval between the last pulse and the second-to-the-last pulse to the initial interval response to the last pulse failing to capture the heart according to the predetermined protocol.

10. The system of claim 1 wherein the implantable cardiac stimulation device includes a telemetry circuit coupled to the processor and wherein the system further includes an external device that communicates with the telemetry circuit and provides the processor with initial pacing intervals.

11. In an implantable cardiac stimulation device, a system for automatically inducing a tachyarrhythmia of a heart for the performance of a test of the heart, the system comprising:

stimulation means for providing groups of stimulation pulses to the heart, the stimulation pulses being separated in time by pulse intervals having durations for overdrive stimulating the heart; and control means for adjusting the durations of the pulse intervals in a prescribed manner after the provision of each group of stimulation pulses to the heart.

12. The system of claim 11 wherein the control means includes means for detecting the tachyarrhythmia of the heart and means for terminating the provision of the stimulation pulses to the heart by the stimulation means when a group of the stimulation pulses has induced the tachyarrhythmia.

13. The system of claim 11 wherein the control means includes means for determining capture of the heart by each delivered stimulation pulse and means for terminating the provision of the stimulation pulses to the heart by the stimulation means when a predetermined number of successive stimulation pulses fail to capture the heart.

14. The system of claim 13 wherein the predetermined number is two.

15. The system of claim 13 wherein the control means requires a minimum pulse interval for determining capture of the heart by a stimulation pulse and further includes means for terminating the provision of the stimulation pulses to the heart by the stimulation means when a pulse interval falls below the minimum pulse interval.

16. The system of claim 11 wherein the control means adjusts the pulse intervals of a last set of stimulation pulses of each group of stimulation pulses in the prescribed manner.

17. The system of claim 11 wherein the control means includes means for determining capture of the heart by each stimulation pulse, wherein each group of stimulation pulses includes a last pulse and a second-to-the-last pulse, and wherein the control means includes means for decrementing the pulse interval between the last pulse and the second-to-the-last pulse responsive to the last pulse capturing the heart.

18. The system of claim 11 wherein the control means includes means for determining capture of the heart by each stimulation pulse, wherein each group of stimulation pulses includes a last pulse, a second-to-the-last pulse, and a third-to-the-last pulse, and wherein the control means includes means for decrementing the pulse interval between the second-to-the-last pulse and the third-to-the-last pulse responsive to the last pulse failing to capture the heart.

19. The system of claim 18 wherein the pulse interval between the last pulse and the second-to-the-last pulse is preset to an initial interval prior to provision of the stimulation pulses to the heart by the stimulation means and wherein the control means further includes means for setting the pulse interval between the last pulse and the second-to-the-last pulse to the initial interval responsive to the last pulse failing to capture the heart.

20. The system of claim 1 wherein the implantable cardiac stimulation device includes telemetry means coupled to the control means and wherein the system further includes external programming means for communicating with the telemetry means and providing the control means with initial pulse intervals.

21. In an implantable cardiac stimulation device, a method of automatically inducing a tachyarrhythmia of a heart for the performance of an electrophysiological test of the heart, the method including the steps of:

storing a predetermined induction protocol in the implantable device;

applying groups of stimulation pulses to the heart, the stimulation pulses being separated in time by interpulse intervals for overdriving the heart; and adjusting the interpulse intervals in accordance with the stored induction protocol after applying each group of stimulation pulses to the heart.

22. The method of claim 21 including the further steps of detecting for the tachyarrhythmia of the heart after applying each group of stimulation pulses to the heart and terminating the application of the stimulation pulses to the heart responsive to detecting the tachyarrhythmia.

23. The system of claim 21 including the further steps of determining capture of the heart by each applied stimulation pulse and terminating the application of the stimulation pulses to the heart when a predetermined number of successive stimulation pulses fail to capture the heart.

24. The method of claim 23 wherein the predetermined number is two.

25. The method of claim 23 wherein the step of determining capture of the heart requires a minimum interpulse interval to determine capture of the heart by a stimulation pulse and wherein the method further includes terminating the application of the stimulation pulses to the heart when an interpulse interval falls below the minimum interpulse interval.

26. The method of claim 21 wherein the adjusting step includes adjusting the interpulse intervals of only a last set of stimulation pulses of each group of stimulation pulses in accordance with the stored induction protocol.

27. The method of claim 21 further including the step of determining capture of the heart by each stimulation pulse, wherein each group of stimulation pulses includes a last pulse and a second-to-the-last pulse, and wherein the method further includes decrementing the interpulse interval between the last pulse and the second-to-the-last responsive to the last pulse capturing the heart.

28. The method of claim 21 including the further step of determining capture of the heart by each stimulation pulse, wherein each group of stimulation pulses includes a last pulse, a second-to-the-last pulse, and a third-to-the-last pulse, and wherein the method further includes the step of decrementing the interpulse interval between the second-to-the-last pulse and the third-to-the-last pulse responsive to the last pulse failing to capture the heart.

29. The method of claim 28 including the further steps of presetting the interpulse interval between the last pulse and the second-to-the-last pulse to an initial interval prior to applying the stimulation pulses to the heart and setting the interpulse interval between the last pulse and the second-to-the-last pulse to the initial interval responsive to the last pulse failing to capture the heart.

30. The method of claim 21 including the further step of setting the interpulse intervals to initial values prior to the applying step.

* * * * *